United States Patent [19]
Rocha et al.

[11] Patent Number: 5,910,441
[45] Date of Patent: Jun. 8, 1999

[54] DNA ENCODING FIBRONECTIN AND FIBRINOGEN BINDING PROTEIN FROM GROUP A STREPTOCOCCI

[75] Inventors: Claudia Rocha, New York; Vincent A. Fischetti, West Hempstead, both of N.Y.

[73] Assignee: The Rockefeller University, New York, N.Y.

[21] Appl. No.: 08/714,402

[22] Filed: Sep. 16, 1996

[51] Int. Cl.$^6$ .............................. C12N 15/00; C12N 5/00; C07H 21/04
[52] U.S. Cl. ...................... 435/320.1; 435/325; 536/23.7
[58] Field of Search ........................ 536/23.7; 435/320.1, 435/325

[56] References Cited

U.S. PATENT DOCUMENTS 4,399,216   8/1983   Axel et al. .
5,416,021   5/1995   Hook et al. .

OTHER PUBLICATIONS

Jaffe et al (Molecular Microbiology vol. 21 No. 2 pp. 373–384 Jul. 1996).
Courtney et al (Infection & Immunity vol. 62 No. 9 pp. 3937–3947 Sep. 1994).
Hoeoek, M., et al. "Fibronectin Binding Protein" Accession No. A12915 (1994) Abstract.
Hoeoek, M., et al. "Fibronectin Binding Protein" Accession No. A12901 (1994) Abstract.
Jonsson, K. et al., "Two Different Ganes Encode Fibronectin Binding Proteins in *Staphylococcus aureus*" *Eur J. Biochem.* (1991) 202:1041–1048.
Kline, J.B., et al., "Identification of a Fibronectin–Binding Protein (GfbA) in Pathogenic Group G Streptococci" *Infect. Immun.* (1996) 64:2122–2129.
Kreikemeyer, B. et al., "Characterization of a Novel Fibronectin–Binding Surface Protein in Group A Streptococci" *Mol. Microbiol.* (1995) 17:137–145.
Lindgren P. et al., "Two Different Genes Coding for Fibronectin–Binding Proteins from *Streptococcus dysgalactiae*", *Eur. J. Biochem.* (1993) 214:819–827.
McDevitt, D. et al., "Molecular Characterization of the Clumping Factor (fibrinogen receptor) of *Staphylococcus aureus*", Mol. Microbiol. (1994) 11:237–248.
Ozeri, V., et al. "A Two–Domain Mechanism for Group A Streptococcal Adherence Through Protein F to the Extrcellular Matrix", *EMBO J.* (1996) 15:989–998.
Rakonjac, J. et al., "DNA Sequence of the Serum Opacity Factor of Group A Streptococci: Identification of a Fibronectin–Binding Repeat Domain", *Infect. Immun.* (1995) 63:622–631.
Talay, S.R. et al., "Fibronectin–Binding Protein of Strptococcus Pyogenes: Sequence of the Binding Domain Involved in Adherence of Strptococci to Epithelial Cells", *Infection and Immunity* (1992) 603837–3844.
Flock, J–I et al. "Cloning and Expression of the Gene for a Fibronectin–Binding Protein from *Staphylococcus aureus*", EMBO J. (1987) 6:2351–2357.
Hanski, E. et al. "Protein F, a Fibronectin–binding Protein, is an Adhesin of the group A Streptococcus *Streptococcus pyogenes*", *Proc. Natl. Acad. Sci. USA* (1992) 89:6172–6176.
Hanski, E. et al., "Expression of Protein F, the Fibronectin–Binding Protein of *Streptococcus pyogenes*JRS4, in Heterologous Streptococcal and Enterococcal Strains Promotes Their Adherence to Respiratory Epithelial Cells", Infect. Immun. (1992) 60:5119–5125.
Lindgren, P. et al., "Cloning and Expression of Two Different Genes from Streptococcus dysgalactiae Encoding Fibronectin Receptors", *J. Biol. Chem.* (1992) 267:1924–1931.
Sela, S. et al. "Protein F: an adhesin of *Streptococcus pyogenes*Binds Findronectin via Two Distinct Domains", *Mol. Microbiol.* (1993) 10:1049–1055.
Signas, C., et al. "Nucleotide Sequence of the Gene for a Fibronectin–binding Protein from *Staphylococcus aureus*: Use of this Peptide Sequence in the Synthesis of Biologically Active Peptides", Proc. Natl. Acad. Sci. USA (1989) 86:699–703.

*Primary Examiner*—Anthony C. Caputa
*Assistant Examiner*—Mark Navarro
*Attorney, Agent, or Firm*—Burns, Doane, Swecker & Mathis, L.L.P.

[57] ABSTRACT

This invention relates to a novel fibrinogen and fibronectin binding protein from group A streptococci, and the DNA encoding the protein. The protein and its DNA are useful in the preparation of compositions for the diagnosis, treatment, and prevention of streptococcal infection.

11 Claims, 5 Drawing Sheets

Figure 2. Northern Blot
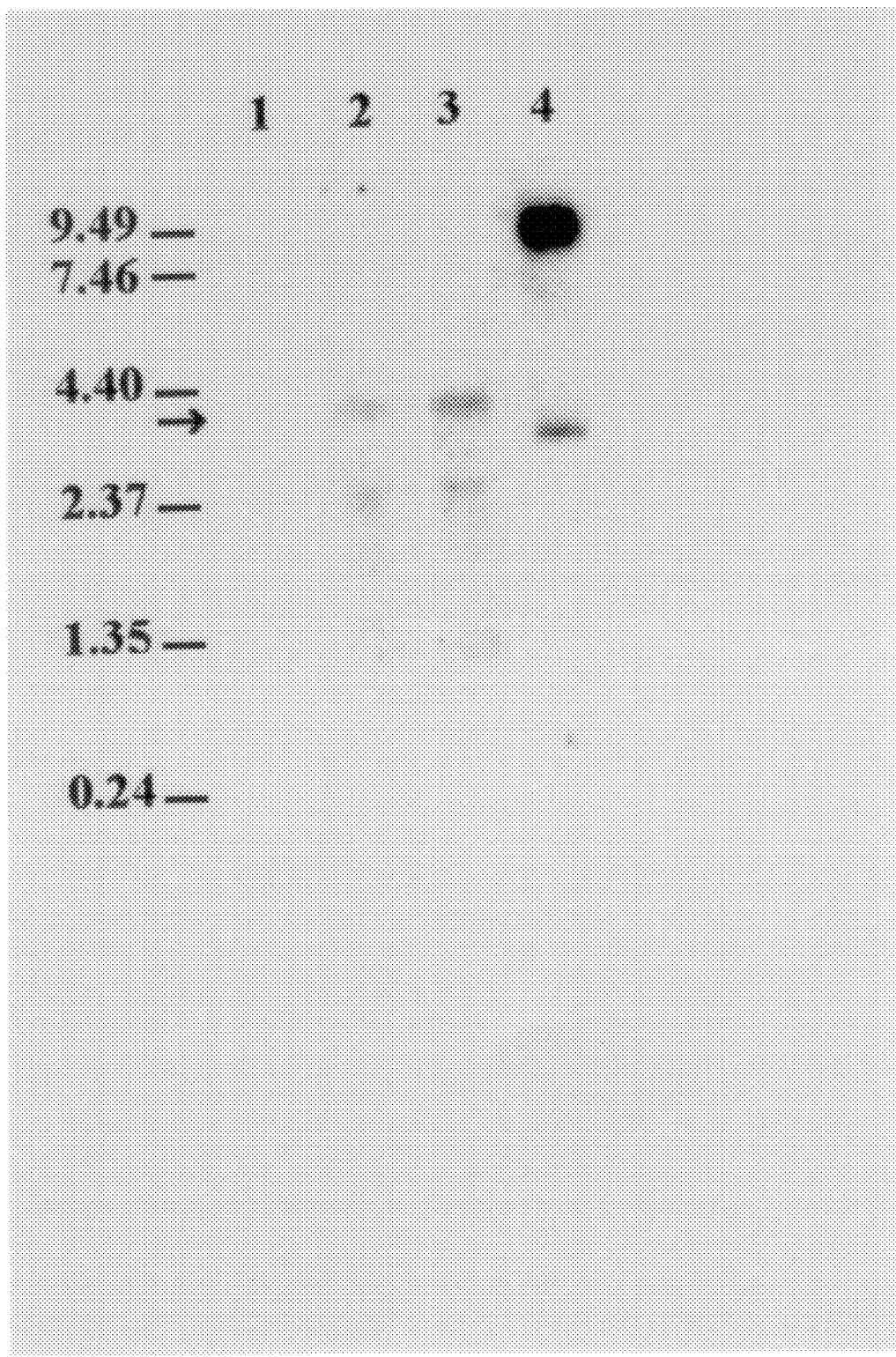

```
         10        20        30        40        50        60        70
GTACGTTAAGCGCTTGAAAAAGAAAGAGTTACAGATAATGACATAAAAAACGATAAAAAACCATCAAAAT    70
AAATACTCTGACCATAAGATGTAGACTTGACAACTGAAAATAGTAAAATAACTATTTGACAGTTGGCCTG   140
TAGTCTTTAGTTTTGGACATAGGCTGTCGCTTATGAATGTGGAGAGAGAAAATAAATGACACAAAAAAAT   210
AGCTATAAGTTAAGCTTCCTGTTATCCCTAACAGGATTTATTTTAGGTTTATTATTGGTTTTTATAGGAT   280
TGACCGGAGTATCAGTAGGACATGCGGAAACAAGAAATGGAGCAAACAAACAAGGATCTTTTGAAATCAA   350
GAAAGTCGACCAAAACAATAAGCCTTTACCGGGAGCAACTTCTTCTCTGACATCAAAGGATGGCAAGGGA   420
ACATCTGTTCAAAGCTTCACTTCAAATGATAAAGGTATTGTAGATGCTCAAAATCTCCAACCAGGGACTT   490
ATACCTTAAAAGAAGAAACAGCACCAGATGGTTATGATAAAACCAGCCGGACTTGGACAGTGACTGTTTA   560
TGAGAACGGCTATACCAAGTTGGTTGAAAATCCCTATAATGGGGAAATCATCAGTAAAGCAGGGTCAAAA   630
GATGTTAGTAGTTCTTTACAGTTGGAAAATCCCAAAATGTCAGTTGTTTCTAAATATGGGAAAACAGAGG   700
TTAGTAGTGGCGCAGCGGATTTCTACCGCAACCATGCCGCCTATTTTAAAATGTCTTTTGAGTTGAAACA   770
AAAGGATAAATCTGAAACAATCAACCCAGGTGATACCTTTGTGTTACAGCTGGATAGACGTCTCAATCCT   840
AAAGGTATCAGTCAAGATATCCCTAAAATCATTTACGACAGTGCAAATAGTCCGCTTGCGATTGGAAAAT   910
ACCATGCTGAGAACCATCAACTTATCTATACTTTCACAGATTATATTGCGGGTTTAGATAAAGTCCAGTT   980
GTCTGCAGAATTGAGCTTATTCCTAGAGAATAAGGAAGTGTTGGAAAATACTAGTATCTCAAATTTTAAG  1050
AGTACCATAGGTGGGCAGGAGATCACCTATAAAGGAACGGTTAATGTTCTTTATGGAAATGAGAGCACTA  1120
AAGAAAGCAATTATATTACTAATGGATTGAGCAATGTGGGTGGGAGTATTGAAAGCTACAACACCGAAAC  1190
GGGAGAATTTGTCTGGTATGTTTATGTCAATCCAAACCGTACCAATATTCCTTATGCGACCATGAATTTA  1260
TGGGGATTTGGAAGGGCTCGTTCAAATACAAGCGACTTAGAAAACGACGCTAATACAAGTAGTGCTGAGC  1330
TTGGAGAGATTCAGGTCTATGAAGTACCTGAAGGAGAAAAATTACCATCAAGTTATGGGGTTGATGTTAC  1400
AAAACTTACTTTAAGAACGGATATCACAGCAGGCCTAGGAAATGGTTTTCAAATGACCAAACGTCAGCGA  1470
ATTGACTTTGGAAATAATATCCAAAATAAAGCATTTATCATCAAAGTAACAGGGAAAACAGACCAATCTG  1540
GTAAGCCATTGGTTGTTCAATCCAATTTGGCAAGTTTTCGTGGTGCTTCTGAATATGCTGCTTTTACTCC  1610
AGTTGGAGGAAATGTCTACTTCCAAAACGAAATTGCCTTGTCTCCTTCTAAGGGTAGTGGTTCTGGGAAA  1680
AGTGAATTTACTAAGCCCTCTATTACAGTAGCAAATCTAAAACGAGTGGCTCAGCTTCGCTTTAAGAAAA  1750
TGTCAACTGACAATGTGCCATTGCCAGAAGCGGCTTTTGAGCTGCGTTCATCAAATGGTAATAGTCAGAA  1820
ATTAGAAGCCAGTTCAAACACACAAGGAGAGGTTCACTTTAAGGACCTGACCTCGGGCACATATGACCTG  1890
TATGAAACAAAAGCGCCAAAAGGTTATCAGCAGGTGACAGAGAAATTGGCGACCGTTACTGTTGATACTA  1960
CCAAACCTGCTGAGGAAATGGTCACTTGGGGAAGCCCACATTCGTCTGTAAAAGTAGAAGCTAACAAAGA  2030
AGTCACGATTGTCAACCATAAAGAAACCCTTACGTTTTCAGGGAAGAAAATTTGGGAGAATGACAGACCA  2100
GATCAACGCCCAGCAAAGATTCAAGTGCAACTGTTGCAAAATGGTCAAAAGATGCCTAACCAGATTCAAG  2170
AAGTAACGAAGGATAACGATTGGTCTTATCACTTCAAAGACTTGCCTAAGTACGATGCCAAGAATCAGGA  2240
```

FIGURE 3A

```
         10        20        30        40        50        60        70
GTATAAGTACTCAGTTGAAGAAGTAAATGTTCCAGACGGCTACAAGGTGTCGTATTTAGGAAATGATATA    2310
TTTAACACCAGAGAAACAGAATTTGTGTTTGAACAGAATAACTTTAACCTTGAATTTGGAAATGCTGAAA    2380
TAAAAGGTCAATCTGGGTCAAAAATCATTGATGAAGACACGCTAACGTCTTTCAAAGGTAAGAAAATTTG   2450
GAAAAATGATACGGCAGAAAATCGTCCCCAAGCCATTCAAGTGCAGCTTTATGCTGATGGAGTGGCTGTG   2520
GAAGGTCAAACCAAATTTATTTCTGGCTCAGGTAATGAGTGGTCATTTGAGTTTAAAAACTTGAAGAAGT   2590
ATAATGGAACAGGTAATGACATCATTTACTCAGTTAAAGAAGTAACTGTTCCAACAGGTTATGATGTGAC   2660
TTACTCAGCTAATGATATTATTAATACCAAACGTGAGGTTATTACACAACAAGGACCGAAACTAGAGATT   2730
GAAGAAACGCTTCCGCTAGAATCAGGTGCTTCAGGCGGTACCACTACTGTCGAAGACTCACGCCCAGTTG   2800
ATACCTTATCAGGTTTATCAAGTGAGCAAGGTCAGTCCGGTGATATGACAATTGAAGAAGATAGTGCTAC   2870
CCATATTAAATTCTCAAAACGTGATATTGACGGCAAAGAGTTAGCTGGTGCAACTATGGAGTTGCGTGAT   2940
TCATCTGGTAAAACTATTAGTACATGGATTTCAGATGGACAAGTGAAAGATTTCTACCTGATGCCAGGAA   3010
AATATACATTTGTCGAAACCGCAGCACCAGACGGTTATGAGATAGCAACTGCTATTACCTTTACAGTTAA   3080
TGAGCAAGGTCAGGTTACTGTAAATGGCAAAGCAACTAAAGGTGACACTCATATTGTCATGGTTGATGCT   3150
TACAAGCCAACTAAGGGTTCAGGTCAGGTTATTGATATTGAAGAAAAGCTTCCAGACGAGCAAGGTCATT   3220
CTGGTTCAACTACTGAAATAGAAGACAGTAAATCTTCAGACCTTATCATTGGCGGTCAAGGTGAAGTTGT   3290
TGACACAACAGAAGACACACAAAGTGGTATGACGGGCCATTCTGGCTCAACTACTGAAATAGAAGATAGC   3360
AAGTCTTCAGACGTTATCATTGGTGGTCAGGGGCAGGTTGTCCAGACAACAGAGGATACCCAAACTGGCA   3430
TGTACGGGGATTCTGGTTGTAAAACGGAAGTCGAAGATACTAAACTAGTACAATCCTTCCACTTTGATAA   3500
CAAGGAACCAGAAAGTAACTCTGAGATTCCT   3531
```

FIGURE 3B

```
         10        20        30        40        50        60        70
|||||||||||||||||||||||||||||||||||||||||||||||||||||||||||||||||||||||||
MTQKNSYKLSFLLSLTGFILGLLLVFIGLTGVSVGHAETRNGANKQGSFEIKKVDQNNKPLPGATSSLTS        70
KDGKGTSVQSFTSNDKGIVDAQNLQPGTYTLKEETAPDGYDKTSRTWTVTVYENGYTKLVENPYNGEIIS       140
KAGSKDVSSSLQLENPKMSVVSKYGKTEVSSGAADFYRNHAAYFKMSFELKQKDKSETINPGDTFVLQLD       210
RRLNPKGISQDIPKIIYDSANSPLAIGKYHAENHQLIYTFTDYIAGLDKVQLSAELSLFLENKEVLENTS       280
ISNFKSTIGGQEITYKGTVNVLYGNESTKESNYITNGLSNVGGSIESYNTETGEFVWYVYVNPNRTNIPY      350
ATMNLWGFGRARSNTSDLENDANTSSAELGEIQVYEVPEGEKLPSSYGVDVTKLTLRTDITAGLGNGFQM       420
TKRQRIDFGNNIQNKAFIIKVTGKTDQSGKPLVVQSNLASFRGASEYAAFTPVGGNVYFQNEIALSPSKG       490
SGSGKSEFTKPSITVANLKRVAQLRFKKMSTDNVPLPEAAFELRSSNGNSQKLEASSNTQGEVHFKDLTS       560
GTYDLYETKAPKGYQQVTEKLATVTVDTTKPAEEMVTWGSPHSSVKVEANNEVTIVNHKETLTFSGKKIW       630
ENDRPDQRPAKIQVQLLQNGQKMPNQIQEVTKDNDWSYHFKDLPKYDAKNQEYKYSVEEVNVPDGYKVSY       700
LGNDIFNTRETEFVFEQNNFNLEFGNAEIKGQSGSKIIDEDTLTSFKGKKIWKNDTAENRPQAIQVQLYA       770
DGVAVEGQTKFISGSGNEWSFEFKNLKKYNGTGNDIIYSVKEVTVPTGYDVTYSANDIINTKREVITQQG       840
PKLEIEETLPLESGASGGTTTVEDSRPVDTLSGLSSEQGQSGDMTIEEDSATHIKFSKRDIDGKELAGAT       910
MELRDSSGKTISTWISDGQVKDFLYMPGKYTFVETAAPDGYEIATAITFTVNEQGQVTVNGKATKGDTHI       980
VMVDAYKPTKGSGQVIDIEEKLPDEQGHSGSTTEIEDSKSSDLIIGGQGEVVDTTEDTQSGMTGHSGSIT      1050
EIEDSKSSDVIIGGQGQVVQTTEDTQTGMYGDSGCKTEVEDTKLVQSFHFDNKEPESNSEIP     1112
```

DNA ENCODING FIBRONECTIN AND FIBRINOGEN BINDING PROTEIN FROM GROUP A STREPTOCOCCI

BACKGROUND OF THE INVENTION

1. Field of the Invention

This invention relates to a novel fibrinogen and fibronectin binding protein from group A streptococci, and the DNA encoding the protein. The protein and its DNA are useful in the preparation of compositions for the diagnosis, treatment, and prevention of streptococcal infection.

2. Description of the Related Art

Among surface proteins of gram-positive bacteria, the fibronectin-binding (Fn-binding) proteins are responsible for adhesion to host epithelial cells (11, 12). Accordingly, Fn-binding proteins may provide the bacterial cell with the means to initiate the infection process (11, 12, 13, 14). Fn-binding proteins have been identified in Staphylococcus aureus (3, 11, 16), class I (SOF) S. pyogenes (10, 12, 15) and Streptococcus dysgalactiae (6, 14). Sequence analysis of these proteins revealed that they are large cell surface proteins, with a predicted size range of 73–122 kDa. The domain architecture of these molecules is similar: a divergent N-terminal portion which constitutes up to 80% of their sequence, followed by three to five homologous tandem Fn-binding repeats of from 32 to 43 residues each (3, 6, 12, 15, 16). In at least two cases, protein F from S. pyogenes class I and FnBPB from S. aureus, a region of approximately 50 residues N terminal to the tandem repeats has also been implicated as essential for maximal Fn-binding activity (3, 15). A putative cell wall-spanning segment is located C terminally to the repeats, followed by a typical gram-positive cell attachment motif.

Group A Streptococci (Streptococcus pyogenes) is the etiologic agent for different suppurative infections (e.g., pharyngitis, impetigo, and necrotizing fasciitis) as well as systemic diseases (e.g., scarlet fever, toxic shock-like syndrome), some of which may lead to serious sequelae, such as rheumatic fever and glomerulonephritis. The ability to bind fibronectin has proven to be one of the mechanisms Streptococcus pyogenes use for attachment to host cells (5, 8, 10). Since this glycoprotein is present in body fluids, extracellular matrices, and on the surface of mammalian cells, the identification and characterization of new fibronectin-binding proteins is likely to have pathogenic significance.

SUMMARY OF THE INVENTION

Accordingly, a major object of the present invention is to provide a new streptococcal fibronectin and fibrinogen binding protein. The present invention also provides compositions of matter, including pharmaceutical compositions, comprising the fibronectin and fibrinogen binding protein of the present invention. The present invention further provides antibodies to the fibronectin and fibrinogen binding protein of the present invention and methods for assaying the proteins of the present invention in biological samples using those antibodies.

A further object of the present invention is to provide the DNA encoding the fibronectin and fibrinogen binding protein of the present invention. The present invention also provides vectors, including plasmids and viral vectors comprising the DNA of the present invention, methods of transforming cells with the vectors of the present invention, and transformed cells.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 2. Northern hybridization with a specific probe for sffbp-12. 10 μg of total RNA was loaded from each sample (1–3), and 5 ng of the control DNA (4). The hybridization solution contained 1×10$^6$ cpm/ml of the $^{32}$P-labeled probe. Lanes: 1) 3 hr culture; 2) 4 hour culture; 3) 5 hr culture; 4) Control: plasmid pBS3.1Q containing the C-terminal half of sffbp-12. The positions of the RNA molecular markers (in kilobases) are shown to the left.

FIG. 3A and 3B [SEQ ID NO.: 1]. Partial nucleotide sequence of sffbp-12.

FIG. 4 [SEQ ID NO.: 2]. Partial amino acid sequence of SFFBP-12.

DETAILED DESCRIPTION OF THE PREFERRED EMBODIMENTS OF THE INVENTION

Figure 1:
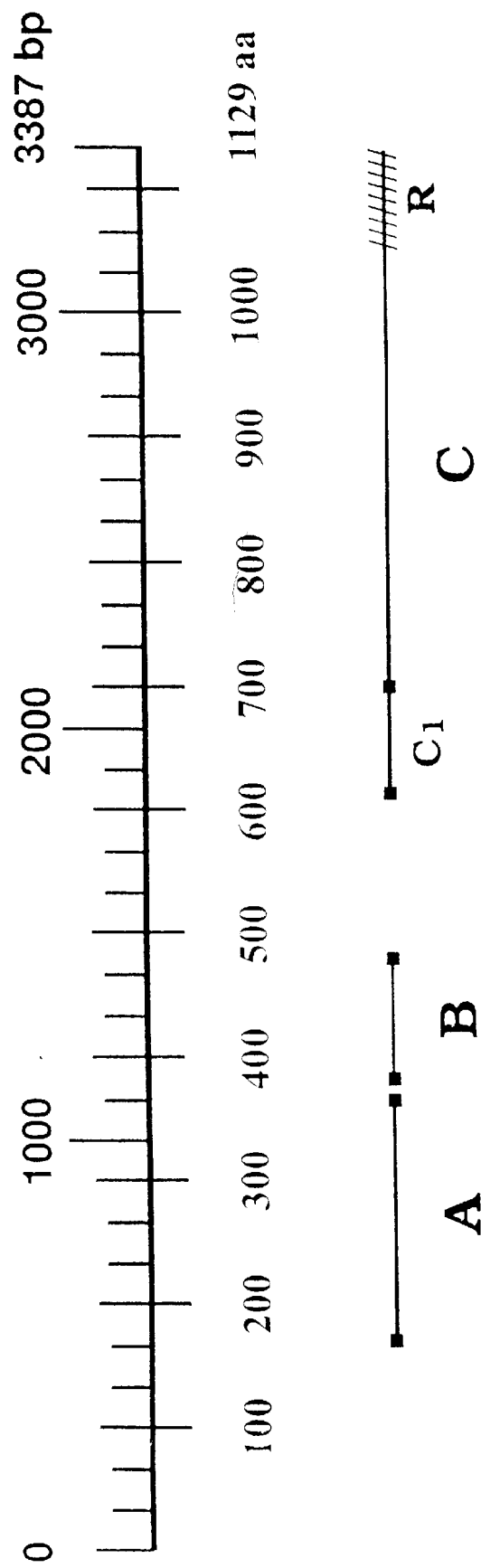
FIG. 1. Map of SFFBP-12 showing the different regions of the protein based on the homology with known fibronectin and fibrinogen binding proteins from streptococci and staphylococci, as well as with the S. aureus collagen adhesin gene.

The present invention relates to a fibrinogen- and fibronectin-binding protein (SFFBP-12) of about 123.8 kDa, comprising an amino acid sequence as shown in FIG. 3. The present invention further relates to the gene encoding the SFFBP-12 protein, termed the sffbp-12 gene, comprising the DNA sequence shown in FIG. 4.

More particularly, the present invention relates to methods for detecting and purifying a fibronectin- and fibrinogen-binding protein from group A streptococci, and also relates to the purified fibronectin- and fibrinogen-binding protein itself.

The sffbp-12 gene encoding the SFFBP-12 fibronectin- and fibrinogen-binding protein can also serve as a hybridization probe to isolate corresponding genes from other species by cross-hybridization under low to moderate stringency conditions. Such conditions are usually found empirically by determining the conditions wherein the probe specifically cross-hybridizes to its counterpart gene with a minimum of background hybridization. Nucleic acid hybridization is a well known technique and thoroughly detailed in Sambrook et al.

As noted above, the DNA encoding the fibronectin- and fibrinogen-binding protein can be originally isolated using PCR. Corresponding DNAs from other species can also be isolated using PCR, and oligonucleotides for performing these subsequent PCR reactions can be optimized using the sequence information obtained from DNA cloned from the first species.

A further aspect of the present invention provides the nucleic acids encoding the subject genes in replicable expression vectors and transformed hosts containing these vectors. The replicable expression vectors may also be used to obtain the polypeptides of the present invention by well known methods in recombinant DNA technology.

The instant replicable expression vectors comprise a nucleic acid encoding the subject gene, i.e., the coding sequence is operably linked in proper reading frame to a nucleotide sequence element which directs expression of the protein. In particular, the nucleotide sequence elements may include a promoter, a transcription enhancer element, a termination signal, a translation signal, or a combination of two or more of these elements, generally including at least a promoter element.

Replicable expression vectors are generally DNA molecules engineered for controlled expression of a desired gene, especially where it is desirable to produce large quantities of a particular gene product, or polypeptide. The vectors comprise one or more nucleotide sequences operably linked to a gene to control expression of that gene, the gene being expressed, and an origin of replication which is operable in the contemplated host. Preferably the vector encodes a selectable marker, for example, antibiotic resistance. Replicable expression vectors can be plasmids, bacteriophages, cosmids and viruses. Any expression vector comprising RNA is also contemplated. The replicable expression vectors of this invention can express the protein at high levels. Many of these vectors are based on pBR322, M13 and lambda and are well known in the art and employ such promoters as trp, lac, $P_L$, T7 polymerase and the like. Hence, one skilled in the art has available many choices of replicable expression vectors, compatible hosts, and well-known methods for making and using the vectors.

Moreover, peptides and fragments as well as chemically modified derivatives of the SFBBP-12 protein are also contemplated by the present invention. Briefly, any peptide fragment, derivative or analog which retains substantially the same fibronectin- and fibrinogen-binding activity of the SFBBP-12 protein is contemplated. An analog may be defined herein as a peptide or fragment which exhibits SFBBP-12 protein fibronectin- and/or fibrinogen-binding activity, but has an amino acid substitution, insertion or deletion in comparison to the wild-type protein. Such an analog can be prepared by the "conservative" substitution of an amino acid having similar chemical properties.

Thus, it should also be appreciated that also within the scope of the present invention are DNA sequences encoding an SFBBP-12 protein having the same amino acid sequence as the wild-type protein, but also those DNA sequences which are degenerate to the wild-type sequence. By "degenerate to" is meant that a different three-letter codon is used to specify a particular amino acid. It is well known in the art that the following codons can be used interchangeably to code for each specific amino acid:

| Amino Acid | Codons |
| --- | --- |
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Termination codon | UAA (ochre) or UAG (amber) or UGA (opal) |

It should be understood that the codons specified above are for RNA sequences. The corresponding codons for DNA have T substituted for U.

Mutations can be made in the wild-type sequence such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein.

The following is one example of various groupings of amino acids:

Amino acids with nonpolar R groups

| | | | | |
| --- | --- | --- | --- | --- |
| Alanine | Valine | Leucine | Isoleucine | Proline |
| Phenylalanine | | Tryptophan | Methionine | |

Amino acids with uncharged polar R groups

| | | | | |
| --- | --- | --- | --- | --- |
| Glycine | Serine | Threonine | Cysteine | Tyrosine |
| Asparagine | Glutamine | | | |

Amino acids with charged polar R groups (negatively charged at Ph 6.0)

Aspartic acid   Glutamic acid

Basic amino acids (positively charged at pH 6.0)

| | | |
| --- | --- | --- |
| Lysine | Arginine | Histidine (at pH 6.0) |

Another grouping may be those amino acids with phenyl groups:

| | | |
| --- | --- | --- |
| Phenylalanine | Tryptophan | Tyrosine |

Another grouping may be according to molecular weight (i.e., size of R groups):

| Amino Acid | Weight | Amino Acid | Weight |
| --- | --- | --- | --- |
| Glycine | 75 | Aspartic acid | 133 |
| Alanine | 89 | Glutamine | 146 |
| Serine | 105 | Lysine | 146 |
| Proline | 115 | Glutamic acid | 147 |
| Valine | 117 | Methionine | 149 |
| Threonine | 119 | Histidine (pH 6.0) | 155 |
| Cysteine | 121 | Phenylalanine | 165 |
| Leucine | 131 | Arginine | 174 |
| Isoleucine | 131 | Tyrosine | 181 |
| Asparagine | 132 | Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and Gln for Asn such that a free $NH_2$ can be maintained.

Amino acid substitutions may also be introduced to substitute an amino acid with a particularly preferable property. For example, a Cys may be introduced at a potential site for disulfide bridging with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Purification of the subject SFFBP-12 fibronectin and fibrinogen binding protein from natural or recombinant sources can be accomplished by conventional purification means such as ammonium sulfate precipitation, gel filtration chromatography, ion exchange chromatography, adsorption chromatography, affinity chromatography, chromatofocusing, HPLC, FPLC, and the like. Where appropriate purification steps can be done in batch or in columns.

Peptide fragments of the SFFBP-12 fibronectin and fibrinogen binding protein can be prepared by proteolysis or by chemical degradation. Typical proteolytic enzymes are trypsin, chymotrypsin, V8 protease, subtilisin and the like; the enzymes are commercially available, and protocols for performing proteolytic digests are well known. Peptide fragments are purified by conventional means, as described above. Peptide fragments can often be identified by amino acid composition or sequence. Peptide fragments are useful as inmunogens to obtain antibodies against the subject SFFBP-12 fibronectin and fibrinogen binding protein.

The present invention also relates to antibodies to the SFFBP-12 fibronectin and fibrinogen binding protein. Such antibodies may be monoclonal or polyclonal and are contemplated as being useful in developing detection assays (immunoassays) for proteins, monitoring protein levels and in purifying protein. Thus, in accordance with this invention, an antibody to an SFFBP-12 fibronectin and fibrinogen binding protein encompasses monoclonal or polyclonal antibodies to said SFFBP-12 fibronectin and fibrinogen binding protein, or to antigenic parts thereof.

Both polyclonal and monoclonal antibodies to the SFFBP-12 fibronectin and fibrinogen binding protein are obtainable by immunization of an animal with purified SFFBP-12 fibronectin and fibrinogen binding protein, purified recombinant SFFBP-12 fibronectin and fibrinogen binding protein, fragments of these proteins, or purified fusion proteins of SFFBP-12 fibronectin and fibrinogen binding protein with another protein. In the case of monoclonal antibodies, partially purified proteins or fragments may serve as immunogens. The methods of obtaining both types of antibodies are well known in the art with excellent protocols for antibody production being found in Harlow et al. (1988) *Antibodies: A Laboratory Manual,* Cold Spring Harbor Laboratory, Cold Spring Harbor, N.Y., 726 pp.

Polyclonal sera are relatively easily prepared by injection of a suitable laboratory animal with an effective amount of the purified SFFBP-12 fibronectin and fibrinogen binding protein, or parts thereof, collecting serum from the animal, and isolating specific sera by any of the known immunoadsorbent techniques. Antibodies produced by this method are useful in virtually any type of immunoassay.

Monoclonal antibodies are particularly useful because they can be produced in large quantities and with a high degree of homogeneity. Hybridoma cell lines which produce monoclonal antibodies are prepared by fusing an immortal cell line with lymphocytes sensitized against the immunogenic preparation and is done by techniques which are well known to those who are skilled in the art. See, e.g., Douillard, I. Y. and Hoffman, T., "Basic Facts About Hybridomas", in *Compendium of Immunology,* Vol. 11, L. Schwartz (Ed.) (1981); Kohler, G. and Milstein, C., *Nature* 256: 495–497 (1975) and *European Journal of Immunology* 6: 511–519 (1976); Harlow et al.; Koprowski, et al., U.S. Pat. No. 4,172,124; Koprowski et al., U.S. Pat. No. 4,196,265 and Wands, U.S. Pat. No. 4,271,145, the teachings of which are herein incorporated by reference.

The presence of the SFFBP-12 fibronectin and fibrinogen binding protein in a sample, such as a culture supernatant and the like, in a microorganism, or in any other source suspected to contain the SFFBP-12 fibronectin and fibrinogen binding protein, can be detected utilizing antibodies prepared as above, either monoclonal or polyclonal, in virtually any type of immunoassay. Likewise, the present antibodies can be used to identify microorganisms which have or produce SFFBP-12 fibronectin and fibrinogen binding protein. Accordingly, the present invention provides a method of detecting an SFFBP-12 fibronectin and fibrinogen binding protein by the steps of contacting a sample suspected of containing said SFFBP-12 fibronectin and fibrinogen binding protein with an antibody of the invention for a time and under conditions sufficient to form an protein-antibody complex and subjecting this complex to a detecting means. As well known to one skilled in the art, the time and conditions for immunodetection assays are variable and depend on the particular assay.

A wide range of detection techniques and conditions are available to one skilled in the art as can be seen by reference to U.S. Pat. Nos. 4,016,043; 4,424,279 and 4,018,653 and to Harlow et al., all of which are incorporated by reference, and which provide extensive protocols for immunodetection of molecules. These techniques, of course, include both single-site and two-site, or "sandwich" assays, assays of the non-competitive types as well as competitive binding assays, ELISA, radioimmunoassays, immunoprecipitation and immunoblotting (Western blotting). Sandwich assays are commonly used, a number of variations of the technique exist, and all are intended to be encompassed by the present invention.

Direct and indirect immunoassays, i.e., ELISA, immunoblotting and the like, may employ reporter molecules linked to either a primary antibody (direct assay) or a second antibody or antibody-specific protein such as Protein A or Protein G (indirect assay). The primary antibody can be an antibody of the subject invention labelled with the desired reporter molecule.

By "reporter molecule," as used herein, is meant a molecule which, by its chemical nature, provides an identifiable signal to detect antigen-antibody complexes. Detection may be either qualitative or quantitative. The most commonly used reporter molecules are either enzymes, fluorophores, or radionuclide containing molecules (i.e., radioisotopes). In the case of an enzyme immunoassay, an enzyme is conjugated to the antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase, and alkaline phosphatase among others. The substrate to be used with a particular enzyme is generally chosen for the production of a detectable color change upon reaction. For example, p-nitrophenyl phosphate is suitable for use with alkaline phosphatase conjugates; for peroxidase conjugates, 1,2-phenylenediamine, 5-aminosalicylic acid, or toluidine are commonly used. It is also possible to employ fluorogenic substrates, which yield a fluorescent product rather than the chromogenic substrates noted above. After binding an enzyme-labeled antibody to an antigen or antigen-antibody complex, as appropriate, the excess labeled antibody is washed away, and a solution containing the appropriate substrate is added. The substrate reacts with the enzyme, i.e., the reporter molecule, to give a qualitative visual signal or a quantitative signal which can be assessed to indicate the amount of antigen present in the sample.

Alternately, fluorescent compounds, such as fluorescein and rhodamine, may be chemically coupled to antibodies without altering their binding capacity. As used in immunofluorescence, when activated by illumination with light of a specific wavelength, a fluorophore-labeled antibody absorbs the light energy, inducing the fluorophore into an excited stated which is followed by emission of light having a characteristic wavelength. Generally, the emitted light is a characteristic color in the visible range and is detectable with a light microscope equipped for immunofluorescence. Fluorescent antibodies are used in sandwich assays, direct and indirect immunoassays as described above, except after washing, the immune complex is exposed to light of the appropriate wavelength, and the fluorescence is observed. Immunofluorescence and enzyme-based immunoassay techniques are both well established in the art and are particularly preferred. However, other reporter molecules, such as radioisotopes, chemiluminescent or bioluminescent molecules, may also be employed. It will be readily apparent to the skilled technician how to vary the procedure to suit the required purpose.

Another aspect of the invention provides a means of purifying an SFFBP-12 fibronectin and fibrinogen binding protein by affinity selection. This method involves contacting a sample containing the SFFBP-12 fibronectin and fibrinogen binding protein with an antibody of the invention, and separating the antigen-antibody complex, e.g., the protein-antibody complex from the remainder of the sample and recovering the protein in a form free from the antibody. Typically the complex-containing sample is fractionated and the fraction(s) containing the—protein are identified by a convenient biochemical, enzymatic, immunological or other detection means. To facilitate fractionation, the subject antibodies can be bound to a chromatography resin before or after binding to the SFFBP-12 protein. This method can yield purified SFFBP-12 protein in large amounts and in pure form.

Accordingly, the present invention is also directed to a kit for the rapid and convenient assay of an SFFBP-12 fibronectin and fibrinogen binding protein, in samples suspected of containing the SFFBP-12 protein. The kit may contain either an antibody directed to the SFFBP-12 fibronectin and fibrinogen binding protein, and a secondary detectable antibody thereto, or may contain a labelled substrate for the protein, such that a labelled fibronectin- or fibrinogen-SFFBP-12 complex is detected in the presence of the SFFBP-12 protein.

Another aspect of the present invention is directed to a method of detecting the DNA or RNA encoding the subject SFFBP-12 fibronectin and fibrinogen binding protein by nucleic acid hybridization techniques such as Southern blotting, Northern blotting and the like, or by the polymerase chain reaction (PCR). Accordingly, a method of detecting a SFFBP-12 protein is provided which comprises contacting a sample suspected of containing said SFFBP-12 protein-encoding DNA with a first nucleic acid sufficiently complementary to hybridize to a second nucleic acid which encodes said protein in said sample for a time and under conditions sufficient to effect said hybridization and thereby form a complex of said first and second nucleic acids and subjecting said complex to a detecting means. In this method, the first nucleic acid may have a reporter group attached thereto. Reporter groups can include radioisotopes, enzymatically detected groups such as biotin or fluorophores such as rhodamine and fluorescein. Detailed methods for hybridization and blotting is found in Sambrook et al.

For PCR, the present method of detecting a gene encoding the SFFBP-12 fibronectin and fibrinogen binding protein comprises subjecting a sample suspected of containing the SFFBP-12 protein to a polymerase chain reaction (PCR) using at least two oligonucleotide primers sufficiently complementary to hybridize to a nucleic acid in said sample which encodes said SFFBP-12 protein, and thereby producing at least one amplified nucleic acid segment and identifying said segment. PCR has been described in U.S. Pat. Nos. 4,683,195; 4,683,202; and 4,800,159, which are incorporated herein by reference as well as described extensively in the literature, see for example Saiki et al. (1988), *Science* 239: 487–491. The segment may be detected by gel electrophoresis or blotting, for example.

Also encompassed by the present invention are inhibitors of the SFFBP-12 fibronectin and fibrinogen binding protein which can be routinely screened using the assay described above.

A still further part of this invention is a pharmaceutical composition of matter for treating or preventing Streptococcus sp. infection with that comprises the SFFBP-12 protein of the present invention or analogs or fragments thereof, mixtures thereof, and/or pharmaceutical salts thereof, and a pharmaceutically-acceptable carrier therefor. Such compositions, when administered to a mammal in need of such treatment, will promote activation of the immune system of the mammal to prevent or ameliorate the effects of streptococcal infection. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

For therapeutic use in a method of treating or prevention streptococcal infection, a protein according to the present invention, or its salt, can be conveniently administered in the form of a pharmaceutical composition containing the protein, or its salt, and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants, and the like. Typically, the carrier may be a solid, liquid, or vaporizable carrier, or combinations thereof. In one preferred embodiment, the composition is a therapeutic composition and the carrier is a pharmaceutically acceptable carrier.

The compound of the invention or its salt may be formulated together with the carrier into any desired unit dosage form. Typical unit dosage forms include tablets, pills, powders, solutions, suspensions, emulsions, granules, capsules, suppositories; injectable solutions and suspensions are particularly preferred.

Each carrier must be "acceptable" in the sense of being compatible with the other ingredients in the formulation and not injurious to the patient. The carrier must be biologically acceptable and inert, i.e., it must permit the immune system of the mammal receiving the protein to be activated by the protein of the present invention.

The protein of the present invention may be administered for therapy by any suitable routes, including topical, oral, rectal, nasal, vaginal and parenteral (including intraperitoneal, subcutaneous, intramuscular, intravenous, intradermal, and transdermal) routes. It will be appreciated that the preferred route will vary with the condition and age of the patient, the nature of the disorder and the chosen active ingredient including other therapeutic agents. Intranasal, oral, and parenteral routes of administration are preferred. However, other routes may also be utilized depending on the conditions of the patient and how long-lasting the treatment is.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further contain anti-oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

The protein of the invention may be present in the composition in an broad proportion to the carrier. For instance, the compound may be present in the amount of 0.01 to 99.9 wt %, and more preferably in about 0.1 to 99 wt %. Still more preferably, the compound may be present in an amount of about 1 to 70 wt % of the composition.

The dosage of the proteins, pharmaceutically acceptable salts thereof, or mixtures thereof, in the compositions of the invention administered to a patient will vary depending on several factors, including, but not limited to, the age, weight, and species of the patient, the general health of the patient, the severity of the symptoms, whether the composition is being administered alone or in combination with antibiotic agents, the incidence of side effects and the like.

In general, a dose suitable for application in the treatment of streptococcal infection is about 0.001 to 100 mg/kg body weight/dose, preferably about 0.01 to 60 mg/kg body weight/dose, and still more preferably about 0.1 to 40 mg/kg body weight/dose per day. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered.

The daily dose may be adjusted taking into account, for example, the above-identified variety of parameters. Typically, the present compositions may be administered in an amount of about 0.001 to 100 mg/kg body weight/day. However, other amounts may also be administered.

To achieve good plasma concentrations, the proteins may be administered, for instance, by intravenous injection of an approximate 0.1 to 1% solution of the active ingredient, optionally in saline, or orally administered as a bolus.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients, including antibiotic compounds and/or therapeutic agents in a pharmaceutical composition. Other therapeutic agents suitable for use herein are any compatible drugs that are effective by the same or other mechanisms for the intended purpose, or drugs that are complementary to those of the present agents. These include agents that are effective for the treatment of streptococcal infections and/or associated conditions in humans.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

The following examples are presented in order to more fully illustrate the preferred embodiments of the invention. They should in no way be construed, however, as limiting the broad scope of the invention.

EXAMPLE 1:

Identification and Characterization of SFFBP-12 Protein and Corresponding sffbp-12 DNA.

A genomic library from an M12 strain was screened using a mono-specific rabbit antiserum against the cell-wall-associated region of the streptococcal M protein. Using this strategy, a gene was identified, which was termed streptococcal fibronectin-fibrinogen binding protein (sffbp-12). The gene encodes a protein (SFFBP-12) of about 123.8 kDa, making it one of the largest proteins of its kind identified for group A streptococci. The translated sequence of sffbp-12 has at the N-terminus a stretch of about 30 hydrophobic amino acids, which may represent a leader peptide. The sequence of the mature protein can be divided into three different regions (A, B, and C) depending on the homology shared with fibronectin-fibrinogen binding proteins previously described in Group A, C, and G streptococci, as well as S. aureus. Region C and the repeated region at the C-terminal end of the molecule exhibit high amino acid sequence identity (69% and 67–75% respectively) with the fibronectin binding protein (FnBB) from S. dysgalactiae (6). N-terminal regions A and B exhibit lower but significant identity (21%) with the fibronectin binding protein (3) and fibrinoger binding protein (clumping factor) from S. aureus (7), respectively (FIG. 1, Table 1). The protein also exhibits the C-terminal LPXTGX motif typical of surface proteins on gram-positive bacteria.

RNA Transcription

To determine if sffbp-12 is in fact transcribed, and at what stage during the growth cycle maximal transcription occurred, a Northern blot was performed on total RNA isolated at different times in the growth cycle (FIG. 2). Hybridization of the blot with a probe specific for the sffbp-12 sequence revealed a band (at 4 and 5 hr of growth) of 3.7 Kb, the expected size of the complete sffbp-12 transcript.

TABLE 1

Homologies of SFFBP-12 With Reported Fibronectin and Fibrinogen Binding Proteins

| | SFFBP-12 | | | | |
|---|---|---|---|---|---|
| | A | B | C | C1 | R |
| S. dysgalactiae Fibronectin-binding protein FnBB (6) | | | 69% | | 67–75%[a] |
| S. aureus Fibronectin binding protein B (3) | | 21% | | | |
| S. equisimilis Fibronectin binding protein | | | 65% | | 50%–60%[e] |
| S. aureus Fibronectin binding protein (pSDF 203) | | | 41% | | 61%[c] |
| S. aureus Fibronectin binding protein | | | 59% | | |
| S. dysgalactie Fibronectin binding protein FnBA | | | 38% | | 70%[c] |
| S. pyogenes Serum Opacity factor (SOF) | | | 45% | | 48%[d] |
| S. pyogenes Fibronectin binding protein II SfbII | | | 45% | | 48%[d] |
| S. pyogenes Fibronectin binding protein II. Sfb (Fn binding domain) | | | 48% | | 48%[b] |
| S. pyogenes Protein F | | | 47% | | 47%[b] |
| Group G Streptococcus Fibronectin-binding protein GfbA | | | 47% | | 47%[b] |
| S. aureus Collagen adhesin | | | | 63% | |
| S. aureus Fibrinogen-binding protein. Clumping factor (7) | | 21% | | | |

[a]: Repeat regions;
[b]: R1 and R2 repeats;
[c]: Half R2 to beginning R3 repeats;
[d]: Part of R3 repeat;
[e]: R1 repeat Summary/Conclusions Fibronectin and fibrinogen-binding proteins have been described as possible adhesin in streptococci and staphylococci. Recent published data have demonstrated that Protein F, a fibronectin-binding protein from group A streptococci, is important in adherence to respiratory cells (8). Other similar proteins already described (i.e., SOF, Sfb and SfbII) are able to competitively inhibit the binding of fibronectin to S. pyogenes (5, 9, 10). Similarly, clumping factor from S. aureus is known to promote adherence to fibrinogen-coated surfaces (7). When the sequence from SFFBP-12 was compared against all other fibronectin and fibrinogen-binding proteins described in streptococci and staphylococci (1–10), an identity at the amino acid level ranging from 38% to 69% was found for the C region. For the repeated region (R), the identity ranged between 47% and 75 %. Unlike all the other proteins already described in group A streptococci, the protein of the present invention, SFFBP-12, shares a high degree of homology (67–75%) with the fibronectin-binding protein B from S. dsgalactiae (6) as well as homology with the S. aureus clumping factor (7) and fibronectin-binding protein B(3), making it a new potential fibronectin-fibrinogen binding protein for group A streptococci. These characteristics would also imply that SFFBP-12 contains two different fibronectin-binding domains, thus enhancing its role as a possible major adhesin molecule. RNA transcription assays showed a transcript with the expected molecular size for the intact SFFBP-12 protein, confirming that the protein is actively expressed during bacterial growth. SFFBP-12 is the largest protein of its kind identified from group A streptococci and is comparable in size to the fibronectin binding protein B from S. dysgalactiae (6). If it is shown that SFFBP-12 does in fact bind both fibronectin and fibrinogen, as the sequence data suggest, it would make this molecule a major virulence determinant for the group A streptococcus.

EXAMPLE 2:

Determination of Fibronectin Binding Activity

The method described in Rakonjac, J. V. et al. *Infect. Immun.* 63:622–631 (1995) is useful to assay fibronectin binding activity. Briefly, recombinant SFFBP-12 protein is prepared from whole-cell lysates of cells transformed with sffbp-12, separated by SDS-PAGE, and electroblotted to nitrocellulose. The blots are then blocked by incubation in 10 mM HEPES (N-2-hydroxyethyl-piperazine-N'-2-ethanesulfonic acid) buffer, containing 150 mM NaCl, 10 mM $MgCl_2$, 2 mM $CaCl_2$, 60 mM KCl, 0.5% Tween 20, 0.04% $NaN_3$, and 0.5% bovine serum albumin, pH 7.4, for 2 to 3 h at room temperature. Subsequently, blots are then probed for 3 to 4 h at room temperature in the same buffer containing $^{125}I$-fibronectin adjusted to $3 \times 10^5$ cpm/ml. Blots are then washed three times with blocking buffer, dried, and exposed to Kodak Blue Brand® film in the presence of an intensifying screen for 24 to 36 h at −70° C.

Radioiodination of fibronectin may be achieved be using Iodobeads® (Pierce Chemical Co., Rockford, Ill.). The labeled protein is separated from free iodine by filtration through Sephadex G-25 (PD-10; Pharmacia LKB Biotechnology, Inc.) and equilibrated in 100 mM phosphate-buffered saline, pH 6.5. The specific activity of the iodinated fibronectin will be approximately $5 \times 10^5$ cpm/µg.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

REFERENCES

The following scientific journal articles illustrate the state of the art, and are incorporated herein by reference:

1. Hoeoek, M., et al. *Accession No.* A12915
2. Hoeoek, M., et al. *Accession No.* A12901.
3. Jonsson, K. et al., *Eur J. Biochem.* 202:1041–1048 (1991).
4. Kline, J. B. et al., *Infect. Immun.* 64:2122–2129 (1996).
5. Kreikemeyer, B., et al., *Mol. Microbiol.* 17:137–145 (1995).
6. Lindgren, P. et al., *Eur. J. Biochem.* 214:819–827 (1993).
7. McDevitt, D., et al. *Mol. Microbiol* 11:237–248 (1994).
8. Ozeri, V., et al. *EMBO J.* 15:989–998 (1996).
9. Rakonjac, J. V. et al. *Infect. Immun.* 63:622–631 (1995).
10. Talay, S. R. et al. *Infect. Immun.* 60:3837–3844 (1992).
11. Flock, J. -I. et al. *EMBO J.* 6:2351–2357 (1987).
12. Hanski, E. et al. *Proc. Natl. Acad. Sci. USA* 89:6271–6176 (1992).
13. Hanski, E. et al. *Infect. Immun.* 60:5119–5125 (1992).
14. Lindgren, P. et al. *J. Biol. Chem.* 267:1924–1931 (1992).
15. Sela, S. et al. *Mol. Microbiol.* 10:1049–1055 (1993).
16. Signas, C. et al. *Proc. Natl. Acad. Sci. USA* 86:699–703 (1989).

What is claimed is:

1. A purified DNA fragment encoding the Streptococcal fibrinogen and fibronectin binding protein (SFFBP-12)(SEQ ID NO: 2).

2. A DNA according to claim 1, wherein the DNA comprises the sequence of the sffbp-12 gene (SEQ ID NO: 1).

3. A replicable expression vector comprising the DNA of claim 1.

4. An isolated host cell transformed with the vector of claim 3.

5. A DNA according to claim 1, operably linked to one or more elements selected from the group consisting of a promoter, a transcription enhancer element, a termination signal, a translation signal, and a combination of two or more of these elements.

6. A DNA according to claim 5, further comprising a selectable marker.

7. A DNA according to claim 1, wherein the DNA consists of the sequence of the sffbp-12 gene (SEQ ID NO: 1).

8. A replicable expression vector comprising the DNA of claim 7.

9. An isolated host cell transformed with a vector according to claim 8.

10. A DNA according to claim 7, further comprising one or more elements selected from the group consisting of a promoter, a transcription enhancer element, a termination signal, a translation signal, and a combination of two or more of these elements.

11. A DNA according to claim 10, further comprising a selectable marker.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3531 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GTACGTTAAG CGCTTGAAAA AGAAAGAGTT ACAGATAATG ACATAAAAAA CGATAAAAAA        60
CCATCAAAAT AAATACTCTG ACCATAAGAT GTAGACTTGA CAACTGAAAA TAGTAAAATA       120
ACTATTTGAC AGTTGGCCTG TAGTCTTTAG TTTTGGACAT AGGCTGTCGC TTATGAATGT       180
GGAGAGAGAA AATAAATGAC ACAAAAAAAT AGCTATAAGT TAAGCTTCCT GTTATCCCTA       240
ACAGGATTTA TTTTAGGTTT ATTATTGGTT TTTATAGGAT TGACCGGAGT ATCAGTAGGA       300
CATGCGGAAA CAAGAAATGG AGCAAACAAA CAAGGATCTT TTGAAATCAA GAAAGTCGAC       360
CAAAACAATA AGCCTTTACC GGGAGCAACT TCTTCTCTGA CATCAAAGGA TGGCAAGGGA       420
ACATCTGTTC AAAGCTTCAC TTCAAATGAT AAAGGTATTG TAGATGCTCA AAATCTCCAA       480
CCAGGGACTT ATACCTTAAA AGAAGAAACA GCACCAGATG GTTATGATAA AACCAGCCGG       540
ACTTGGACAG TGACTGTTTA TGAGAACGGC TATACCAAGT TGGTTGAAAA TCCCTATAAT       600
GGGGAAATCA TCAGTAAAGC AGGGTCAAAA GATGTTAGTA GTTCTTTACA GTTGGAAAAT       660
CCCAAAATGT CAGTTGTTTC TAAATATGGG AAAACAGAGG TTAGTAGTGG CGCAGCGGAT       720
TTCTACCGCA ACCATGCCGC CTATTTTAAA ATGTCTTTTG AGTTGAAACA AAAGGATAAA       780
TCTGAAACAA TCAACCCAGG TGATACCTTT GTGTTACAGC TGGATAGACG TCTCAATCCT       840
AAAGGTATCA GTCAAGATAT CCCTAAAATC ATTTACGACA GTGCAAATAG TCCGCTTGCG       900
ATTGGAAAAT ACCATGCTGA GAACCATCAA CTTATCTATA CTTTCACAGA TTATATTGCG       960
GGTTTAGATA AGTCCAGTT GTCTGCAGAA TTGAGCTTAT TCCTAGAGAA TAAGGAAGTG      1020
TTGGAAAATA CTAGTATCTC AAATTTTAAG AGTACCATAG GTGGGCAGGA GATCACCTAT      1080
AAAGGAACGG TTAATGTTCT TTATGGAAAT GAGAGCACTA AGAAAGCAA TTATATTACT       1140
AATGGATTGA GCAATGTGGG TGGGAGTATT GAAAGCTACA ACACCGAAAC GGGAGAATTT      1200
GTCTGGTATG TTTATGTCAA TCCAAACCGT ACCAATATTC CTTATGCGAC CATGAATTTA      1260
TGGGGATTTG GAAGGGCTCG TTCAAATACA AGCGACTTAG AAAACGACGC TAATACAAGT      1320
AGTGCTGAGC TTGGAGAGAT TCAGGTCTAT GAAGTACCTG AAGGAGAAAA ATTACCATCA      1380
AGTTATGGGG TTGATGTTAC AAAACTTACT TTAAGAACGG ATATCACAGC AGGCCTAGGA      1440
AATGGTTTTC AAATGACCAA ACGTCAGCGA ATTGACTTTG GAAATAATAT CCAAAATAAA      1500
GCATTTATCA TCAAAGTAAC AGGGAAAACA GACCAATCTG GTAAGCCATT GGTTGTTCAA      1560
TCCAATTTGG CAAGTTTTCG TGGTGCTTCT GAATATGCTG CTTTTACTCC AGTTGGAGGA      1620
AATGTCTACT TCCAAAACGA AATTGCCTTG TCTCCTTCTA AGGGTAGTGG TTCTGGGAAA      1680
AGTGAATTTA CTAAGCCCTC TATTACAGTA GCAAATCTAA AACGAGTGGC TCAGCTTCGC      1740
TTTAAGAAAA TGTCAACTGA CAATGTGCCA TTGCCAGAAG CGGCTTTTGA GCTGCGTTCA      1800
```

-continued

```
TCAAATGGTA ATAGTCAGAA ATTAGAAGCC AGTTCAAACA CACAAGGAGA GGTTCACTTT     1860

AAGGACCTGA CCTCGGGCAC ATATGACCTG TATGAAACAA AAGCGCCAAA AGGTTATCAG     1920

CAGGTGACAG AGAAATTGGC GACCGTTACT GTTGATACTA CCAAACCTGC TGAGGAAATG     1980

GTCACTTGGG GAAGCCCACA TTCGTCTGTA AAAGTAGAAG CTAACAAAGA AGTCACGATT     2040

GTCAACCATA AAGAAACCCT TACGTTTTCA GGGAAGAAAA TTTGGGAGAA TGACAGACCA     2100

GATCAACGCC CAGCAAAGAT TCAAGTGCAA CTGTTGCAAA ATGGTCAAAA GATGCCTAAC     2160

CAGATTCAAG AAGTAACGAA GGATAACGAT TGGTCTTATC ACTTCAAAGA CTTGCCTAAG     2220

TACGATGCCA AGAATCAGGA GTATAAGTAC TCAGTTGAAG AAGTAAATGT TCCAGACGGC     2280

TACAAGGTGT CGTATTTAGG AAATGATATA TTTAACACCA GAGAAACAGA ATTTGTGTTT     2340

GAACAGAATA ACTTTAACCT TGAATTTGGA AATGCTGAAA TAAAAGGTCA ATCTGGGTCA     2400

AAAATCATTG ATGAAGACAC GCTAACGTCT TTCAAAGGTA AGAAAATTTG GAAAAATGAT     2460

ACGGCAGAAA ATCGTCCCCA AGCCATTCAA GTGCAGCTTT ATGCTGATGG AGTGGCTGTG     2520

GAAGGTCAAA CCAAATTTAT TTCTGGCTCA GGTAATGAGT GGTCATTTGA GTTTAAAAAC     2580

TTGAAGAAGT ATAATGGAAC AGGTAATGAC ATCATTTACT CAGTTAAAGA AGTAACTGTT     2640

CCAACAGGTT ATGATGTGAC TTACTCAGCT AATGATATTA TTAATACCAA ACGTGAGGTT     2700

ATTACACAAC AAGGACCGAA ACTAGAGATT GAAGAAACGC TTCCGCTAGA ATCAGGTGCT     2760

TCAGGCGGTA CCACTACTGT CGAAGACTCA CGCCCAGTTG ATACCTTATC AGGTTTATCA     2820

AGTGAGCAAG GTCAGTCCGG TGATATGACA ATTGAAGAAG ATAGTGCTAC CCATATTAAA     2880

TTCTCAAAAC GTGATATTGA CGGCAAAGAG TTAGCTGGTG CAACTATGGA GTTGCGTGAT     2940

TCATCTGGTA AAACTATTAG TACATGGATT TCAGATGGAC AAGTGAAAGA TTTCTACCTG     3000

ATGCCAGGAA AATATACATT TGTCGAAACC GCAGCACCAG ACGGTTATGA GATAGCAACT     3060

GCTATTACCT TTACAGTTAA TGAGCAAGGT CAGGTTACTG TAAATGGCAA AGCAACTAAA     3120

GGTGACACTC ATATTGTCAT GGTTGATGCT TACAAGCCAA CTAAGGGTTC AGGTCAGGTT     3180

ATTGATATTG AAGAAAAGCT TCCAGACGAG CAAGGTCATT CTGGTTCAAC TACTGAAATA     3240

GAAGACAGTA AATCTTCAGA CCTTATCATT GGCGGTCAAG GTGAAGTTGT TGACACAACA     3300

GAAGACACAC AAAGTGGTAT GACGGGCCAT TCTGGCTCAA CTACTGAAAT AGAAGATAGC     3360

AAGTCTTCAG ACGTTATCAT TGGTGGTCAG GGGCAGGTTG TCCAGACAAC AGAGGATACC     3420

CAAACTGGCA TGTACGGGGA TTCTGGTTGT AAAACGGAAG TCGAAGATAC TAAACTAGTA     3480

CAATCCTTCC ACTTTGATAA CAAGGAACCA GAAAGTAACT CTGAGATTCC T             3531
```

(2) INFORMATION FOR SEQ ID NO:2:

(i) SEQUENCE CHARACTERISTICS:
        (A) LENGTH: 1112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Thr Gln Lys Asn Ser Tyr Lys Leu Ser Phe Leu Leu Ser Leu Thr
 1               5                  10                  15

Gly Phe Ile Leu Gly Leu Leu Leu Val Phe Ile Gly Leu Thr Gly Val
            20                  25                  30

Ser Val Gly His Ala Glu Thr Arg Asn Gly Ala Asn Lys Gln Gly Ser
        35                  40                  45
```

-continued

```
Phe Glu Ile Lys Lys Val Asp Gln Asn Asn Lys Pro Leu Pro Gly Ala
 50                  55                  60
Thr Ser Ser Leu Thr Ser Lys Asp Gly Lys Gly Thr Ser Val Gln Ser
 65                  70                  75                  80
Phe Thr Ser Asn Asp Lys Gly Ile Val Asp Ala Gln Asn Leu Gln Pro
                 85                  90                  95
Gly Thr Tyr Thr Leu Lys Glu Glu Thr Ala Pro Asp Gly Tyr Asp Lys
                100                 105                 110
Thr Ser Arg Thr Trp Thr Val Thr Val Tyr Glu Asn Gly Tyr Thr Lys
            115                 120                 125
Leu Val Glu Asn Pro Tyr Asn Gly Glu Ile Ile Ser Lys Ala Gly Ser
        130                 135                 140
Lys Asp Val Ser Ser Leu Gln Leu Glu Asn Pro Lys Met Ser Val
145                 150                 155                 160
Val Ser Lys Tyr Gly Lys Thr Glu Val Ser Ser Gly Ala Ala Asp Phe
                165                 170                 175
Tyr Arg Asn His Ala Ala Tyr Phe Lys Met Ser Phe Glu Leu Lys Gln
            180                 185                 190
Lys Asp Lys Ser Glu Thr Ile Asn Pro Gly Asp Thr Phe Val Leu Gln
        195                 200                 205
Leu Asp Arg Arg Leu Asn Pro Lys Gly Ile Ser Gln Asp Ile Pro Lys
    210                 215                 220
Ile Ile Tyr Asp Ser Ala Asn Ser Pro Leu Ala Ile Gly Lys Tyr His
225                 230                 235                 240
Ala Glu Asn His Gln Leu Ile Tyr Thr Phe Thr Asp Tyr Ile Ala Gly
                245                 250                 255
Leu Asp Lys Val Gln Leu Ser Ala Glu Leu Ser Leu Phe Leu Glu Asn
            260                 265                 270
Lys Glu Val Leu Glu Asn Thr Ser Ile Ser Asn Phe Lys Ser Thr Ile
        275                 280                 285
Gly Gly Gln Glu Ile Thr Tyr Lys Gly Thr Val Asn Val Leu Tyr Gly
    290                 295                 300
Asn Glu Ser Thr Lys Glu Ser Asn Tyr Ile Thr Asn Gly Leu Ser Asn
305                 310                 315                 320
Val Gly Gly Ser Ile Glu Ser Tyr Asn Thr Glu Thr Gly Glu Phe Val
                325                 330                 335
Trp Tyr Val Tyr Val Asn Pro Asn Arg Thr Asn Ile Pro Tyr Ala Thr
            340                 345                 350
Met Asn Leu Trp Gly Phe Gly Arg Ala Arg Ser Asn Thr Ser Asp Leu
        355                 360                 365
Glu Asn Asp Ala Asn Thr Ser Ser Ala Glu Leu Gly Glu Ile Gln Val
    370                 375                 380
Tyr Glu Val Pro Glu Gly Glu Lys Leu Pro Ser Ser Tyr Gly Val Asp
385                 390                 395                 400
Val Thr Lys Leu Thr Leu Arg Thr Asp Ile Thr Ala Gly Leu Gly Asn
                405                 410                 415
Gly Phe Gln Met Thr Lys Arg Gln Arg Ile Asp Phe Gly Asn Asn Ile
            420                 425                 430
Gln Asn Lys Ala Phe Ile Ile Lys Val Thr Gly Lys Thr Asp Gln Ser
        435                 440                 445
Gly Lys Pro Leu Val Val Gln Ser Asn Leu Ala Ser Phe Arg Gly Ala
    450                 455                 460
Ser Glu Tyr Ala Ala Phe Thr Pro Val Gly Gly Asn Val Tyr Phe Gln
465                 470                 475                 480
```

```
Asn Glu Ile Ala Leu Ser Pro Ser Lys Gly Ser Gly Ser Gly Lys Ser
            485                 490                 495

Glu Phe Thr Lys Pro Ser Ile Thr Val Ala Asn Leu Lys Arg Val Ala
            500                 505                 510

Gln Leu Arg Phe Lys Lys Met Ser Thr Asp Asn Val Pro Leu Pro Glu
            515                 520                 525

Ala Ala Phe Glu Leu Arg Ser Ser Asn Gly Asn Ser Gln Lys Leu Glu
            530                 535                 540

Ala Ser Ser Asn Thr Gln Gly Glu Val His Phe Lys Asp Leu Thr Ser
545                 550                 555                 560

Gly Thr Tyr Asp Leu Tyr Glu Thr Lys Ala Pro Lys Gly Tyr Gln Gln
            565                 570                 575

Val Thr Glu Lys Leu Ala Thr Val Thr Val Asp Thr Thr Lys Pro Ala
            580                 585                 590

Glu Glu Met Val Thr Trp Gly Ser Pro His Ser Ser Val Lys Val Glu
            595                 600                 605

Ala Asn Asn Glu Val Thr Ile Val Asn His Lys Glu Thr Leu Thr Phe
            610                 615                 620

Ser Gly Lys Lys Ile Trp Glu Asn Asp Arg Pro Asp Gln Arg Pro Ala
625                 630                 635                 640

Lys Ile Gln Val Gln Leu Leu Gln Asn Gly Gln Lys Met Pro Asn Gln
            645                 650                 655

Ile Gln Glu Val Thr Lys Asp Asn Asp Trp Ser Tyr His Phe Lys Asp
            660                 665                 670

Leu Pro Lys Tyr Asp Ala Lys Asn Gln Glu Tyr Lys Tyr Ser Val Glu
            675                 680                 685

Glu Val Asn Val Pro Asp Gly Tyr Lys Val Ser Tyr Leu Gly Asn Asp
            690                 695                 700

Ile Phe Asn Thr Arg Glu Thr Glu Phe Val Phe Glu Gln Asn Asn Phe
705                 710                 715                 720

Asn Leu Glu Phe Gly Asn Ala Glu Ile Lys Gly Gln Ser Gly Ser Lys
            725                 730                 735

Ile Ile Asp Glu Asp Thr Leu Thr Ser Phe Lys Gly Lys Lys Ile Trp
            740                 745                 750

Lys Asn Asp Thr Ala Glu Asn Arg Pro Gln Ala Ile Gln Val Gln Leu
            755                 760                 765

Tyr Ala Asp Gly Val Ala Val Glu Gly Gln Thr Lys Phe Ile Ser Gly
            770                 775                 780

Ser Gly Asn Glu Trp Ser Phe Glu Phe Lys Asn Leu Lys Lys Tyr Asn
785                 790                 795                 800

Gly Thr Gly Asn Asp Ile Ile Tyr Ser Val Lys Glu Val Thr Val Pro
            805                 810                 815

Thr Gly Tyr Asp Val Thr Tyr Ser Ala Asn Asp Ile Ile Asn Thr Lys
            820                 825                 830

Arg Glu Val Ile Thr Gln Gln Gly Pro Lys Leu Glu Ile Glu Thr
            835                 840                 845

Leu Pro Leu Glu Ser Gly Ala Ser Gly Gly Thr Thr Thr Val Glu Asp
            850                 855                 860

Ser Arg Pro Val Asp Thr Leu Ser Gly Leu Ser Ser Glu Gln Gly Gln
865                 870                 875                 880

Ser Gly Asp Met Thr Ile Glu Glu Asp Ser Ala Thr His Ile Lys Phe
            885                 890                 895

Ser Lys Arg Asp Ile Asp Gly Lys Glu Leu Ala Gly Ala Thr Met Glu
```

-continued

```
                    900                 905                 910
  Leu Arg Asp Ser Ser Gly Lys Thr Ile Ser Thr Trp Ile Ser Asp Gly
          915                 920                 925

Gln Val Lys Asp Phe Leu Tyr Met Pro Gly Lys Tyr Thr Phe Val Glu
          930                 935                 940

Thr Ala Ala Pro Asp Gly Tyr Glu Ile Ala Thr Ala Ile Thr Phe Thr
  945                 950                 955                 960

Val Asn Glu Gln Gly Gln Val Thr Val Asn Gly Lys Ala Thr Lys Gly
                  965                 970                 975

Asp Thr His Ile Val Met Val Asp Ala Tyr Lys Pro Thr Lys Gly Ser
              980                 985                 990

Gly Gln Val Ile Asp Ile Glu Glu Lys Leu Pro Asp Glu Gln Gly His
          995                 1000                1005

Ser Gly Ser Thr Thr Glu Ile Glu Asp Ser Lys Ser Ser Asp Leu Ile
          1010                1015                1020

Ile Gly Gly Gln Gly Glu Val Val Asp Thr Thr Glu Asp Thr Gln Ser
  1025                1030                1035                1040

Gly Met Thr Gly His Ser Gly Ser Thr Thr Glu Ile Glu Asp Ser Lys
                  1045                1050                1055

Ser Ser Asp Val Ile Ile Gly Gly Gln Gly Gln Val Val Gln Thr Thr
                  1060                1065                1070

Glu Asp Thr Gln Thr Gly Met Tyr Gly Asp Ser Gly Cys Lys Thr Glu
          1075                1080                1085

Val Glu Asp Thr Lys Leu Val Gln Ser Phe His Phe Asp Asn Lys Glu
          1090                1095                1100

Pro Glu Ser Asn Ser Glu Ile Pro
  1105                1110
```